United States Patent
Chang

(10) Patent No.: US 8,846,621 B2
(45) Date of Patent: Sep. 30, 2014

(54) COMPOSITIONS AND METHODS FOR TREATING DISEASES ASSOCIATED WITH ANGIOGENESIS AND INFLAMMATION

(76) Inventor: Chiwen Chang, Cambridge (GB)

( * ) Notice: Subject to any disclaimer, the term of this patent is extended or adjusted under 35 U.S.C. 154(b) by 0 days.

(21) Appl. No.: 12/628,592

(22) Filed: Dec. 1, 2009

(65) Prior Publication Data

US 2010/0087378 A1 Apr. 8, 2010

Related U.S. Application Data

(63) Continuation of application No. 11/963,912, filed on Dec. 24, 2007, now abandoned, and a continuation-in-part of application No. 11/208,288, filed on Aug. 18, 2005, now abandoned.

(60) Provisional application No. 60/605,013, filed on Aug. 26, 2004.

(51) Int. Cl.
| | | |
|---|---|---|
| *A61K 38/00* | (2006.01) | |
| *A61K 38/43* | (2006.01) | |
| *C07K 14/47* | (2006.01) | |
| *C07K 14/705* | (2006.01) | |
| *C12N 9/00* | (2006.01) | |
| *C07K 16/28* | (2006.01) | |
| *A61K 39/00* | (2006.01) | |

(52) U.S. Cl.
CPC ....... *C07K 14/70596* (2013.01); *C07K 16/2896* (2013.01); *C07K 2316/96* (2013.01); *A61K 2039/505* (2013.01)
USPC ....... 514/16.6; 514/13.1; 424/96.64; 530/350

(58) Field of Classification Search
None
See application file for complete search history.

(56) References Cited

U.S. PATENT DOCUMENTS

| | | | | |
|---|---|---|---|---|
| 5,194,596 | A * | 3/1993 | Tischer et al. | 530/399 |
| 5,712,380 | A * | 1/1998 | Kendall et al. | 536/23.5 |
| 6,265,551 | B1 * | 7/2001 | Duke-Cohan et al. | 530/389.6 |
| 6,534,626 | B1 * | 3/2003 | Oravecz et al. | 530/300 |

FOREIGN PATENT DOCUMENTS

| | | | |
|---|---|---|---|
| WO | WO 97/44453 | * | 11/1997 |
| WO | WO 99/47152 | * | 9/1999 |

OTHER PUBLICATIONS

Machens et al, J Surgical Research 111: 136-142, 2003.*
Ahmad et al, Circ Res 95: 884-891, 2004.*
Cheng et al, J Biol Chem 273(37): 24207-24215, 1998.*
Chica et al, Curr Opin Biotechnol 16(4):378-84, Aug. 2005.*
Witkowski et al, Biochemistry 38(36): 11643-50, Sep. 7, 1999.*
Seffernick et al, J Bacteriol 183 (8): 2405-10, Apr. 2001.*
Cogburn et al., Journal of Nutrition 119:1213-1222,1989.*
Benjamin et al, Development 125:1591-1598, 1998.*
Banks et al., Molecular Human Reproduction 4(4): 377-386, 1998.*
Seffernick et al., J Bacteriol 183 (8): 2405-10, Apr. 2001.*
Jones et al., Pharmacogenomics Journal, 1:126-134, 2001.*
Tosatto et al., Current Pharmaceutical Design, 12:2067-2086, 2006.*

* cited by examiner

*Primary Examiner* — Phuong Huynh
(74) *Attorney, Agent, or Firm* — Hsiu-Ming Saunders; Intellectual Property Connections, Inc.

(57) ABSTRACT

Pharmaceutical compositions and methods for treating diseases associated with angiogenesis and inflammation. The invention relates to a pharmaceutical composition that includes a therapeutically effective amount of sCD26 and/or a biologically active derivative thereof and a pharmaceutically acceptable carrier. The composition may further include a therapeutically effective amount of sFlt-1 and/or a biologically active derivative thereof. Additionally, the invention relates to methods for treating a disease associated with and/or progresses by an inflammatory cytokine-associated inflammation and/or VEGF-associated angiogenesis.

7 Claims, 8 Drawing Sheets

IL-2: APTSSSTKKTQLQLE......

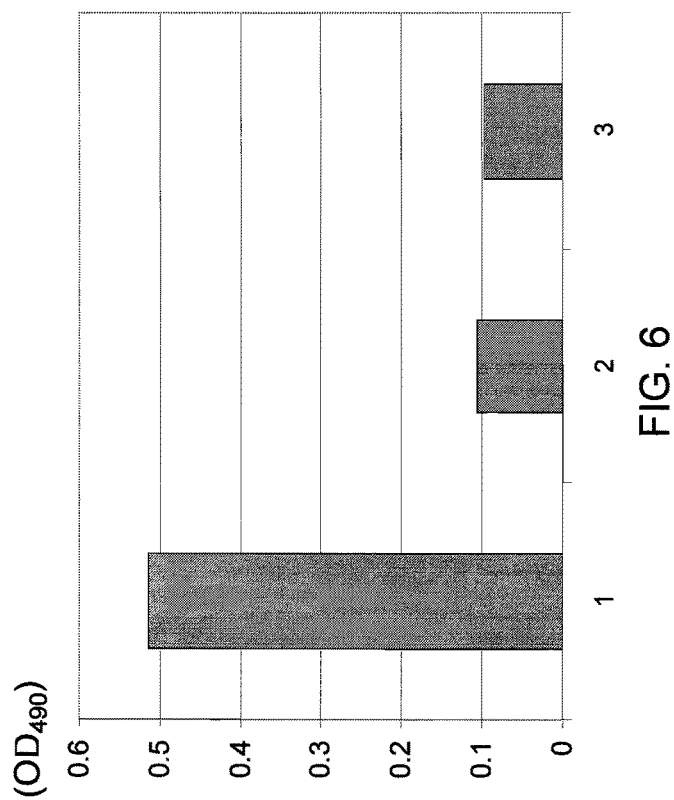

COMPOSITIONS AND METHODS FOR TREATING DISEASES ASSOCIATED WITH ANGIOGENESIS AND INFLAMMATION

CROSS-REFERENCE TO RELATED PATENT APPLICATION

This application is a continuation application, and claims the benefit of U.S. patent application Ser. No. 11/963,912, filed Dec. 24, 2007, entitled "COMPOSITIONS AND METHODS FOR TREATING DISEASES ASSOCIATED WITH ANGIOGENESIS AND INFLAMMATION," the disclosure of which is hereby incorporated herein by reference in its entirety, which is a continuation-in-part application, and claims benefit of U.S. patent application Ser. No. 11/208,288, filed Aug. 18, 2005, entitled "USE OF SOLUBLE CD26 AS INHIBITOR OF ANGIOGENESIS AND INFLAMMATION," by Chiwen Chang, the disclosure of which is hereby incorporated herein by reference in its entirety. The application Ser. No. 11/208,288 claims the benefit, pursuant to 35 U.S.C. §119(e), of U.S. provisional patent application Ser. No. 60/605,013 filed Aug. 26, 2004, which is incorporated herein by reference in its entirety.

FIELD OF THE INVENTION

The present invention relates generally to inhibitors of angiogenesis and inflammatory cytokines, and more specifically to pharmaceutical compositions for treating diseases or disorders associated with angiogenesis and inflammation.

BACKGROUND OF THE INVENTION

Angiogenesis is the formation of new blood vessels by sprouting from pre-existing ones. (Weinstate-Saslow, The FASEB Journal 8: 402-407, 1994; Folkman et al., Science 235: 442-447, 1987). The generation of new blood vessels involves a multistep process, which includes the migration of vascular endothelial cells into tissue, followed by the condensation of such endothelial cells into vessels. Angiogenesis may be induced by an angiogenic agent or be the result of a natural condition. The process is essential to a variety of normal body activities, such as embryo implantation; embryogenesis and development; and wound healing. The process involves a complex interplay of molecules that stimulate and molecules that inhibit the growth and migration of endothelial cells, the primary cells of the capillary blood vessels. (Folkman and Shing, J. Biol. Chem., 267 (16): 10931-34, 1989; Folkman and Klagsbrun, Science, 235, 442-47, 1987).

Several angiogenic agents have been identified. (Hanahan and Folkman, Cell, 86 (3): 353-364, 1996). For example, a number of growth factors have been identified which promote/activate endothelial cells to undergo angiogenesis. These include, by example and not by way of limitation; vascular endothelial growth factor (VEGF); transforming growth factor (TGFβ); acidic and basic fibroblast growth factor (aFGF and bFGF): and platelet derived growth factor (PDGF) (Ferrara and Davis-Smyth, Endocr Rev. 18 (1): 4-25, 1997). VEGF is believed to be a central mediator of angiogenesis. Antibodies directed against VEGF have been shown to suppress tumor growth in vivo and decrease the density of blood vessels in experimental tumors (Kim et al., Nature 362: 841-844, 1993), indicating that VEGF antagonists could have therapeutic applications as inhibitors of tumor-induced angiogenesis.

Normal angiogenic activity is low in healthy adults and limited to certain organs such as the uterus during pregnancy or intensely exercising skeletal muscle. However, its activity increases during injury and in diseases such as cancer, retinopathy, or arthritis, where it contributes to pathological changes. Therefore, angiogenesis can have both the beneficial effects such as facilitating wound healing, and detrimental effects by causing inflammatory diseases such as, for example, rheumatoid arthritis, macular degeneration, psoriasis, and diabetic retinopathy.

Furthermore, it has been shown that angiogenesis is essential for the growth of solid tumors and for tumor metastasis (Bouck et al., Adv Cancer Res.; 69: 135-74, 1996; Yancopoulos et al., Nature 407 (6801): 242-8, 2000). Tumor-induced angiogenesis is initiated by growth factors and cytokines that are released from the tumor or from inflammatory cell infiltrates (Brown et al., Am. J. Path. 143: 1255, 1993; Brown et al., Human Path. 26: 86, 1995; Leek et al., J. Leukocyte Biol. 56: 423, 1994; Hatva et al., Am. J. Pathol. 146: 368, 1995; and Plate et al., Nature 359: 845, 1992). Growth factors and cytokines which are expressed by tumor cells stimulate angiogenesis in a number of animal models including the chick chorioallantoic membrane model, the corneal pocket angiogenesis model, and models involving spontaneous and xenotransplanted tumor growth (Brooks et al., Cell 79: 1157, 1994; Brooks et al., Science 264: 569, 1994; Brooks et al., J. Clin. Invest. 96: 1815, 1995; and Friedlander et al., Science 27: 1500, 1995). Accordingly, tumor-associated angiogenesis is a potential target for therapies that inhibit tumor proliferation, invasion, and metastasis since angiogenesis has been implicated not only in the growth of tumors but also in their metastasis (Liotta et al., 1991, Cell 64: 327; Weinstat-Saslow et al., FASEB J 8: 401, 1994; Blood et al., Biochim. Biophys. Acta 1032: 89, 1990; Folkman, Semin. Cancer Biol. 3: 65, 1992; and Weidner et al., N. Engl. J. Med. 324: 1, 1991).

It has been well recognized that angiogenesis is involved in a variety of diseases or disorders and that such diseases or conditions can be treated by administration of angiogenesis inhibitors. Examples of pathological conditions involving angiogenesis include, but are not limited to, macular degeneration, ocular neovascular glaucoma, diabetic retinopathy, corneal graft rejection, vitamin A deficiency, Sjorgen's disease, acne rosacea, mycobacterium infections, bacterial and fungal ulcers, Herpes simplex infections, systemic lupus, rheumatoid arthritis, osteoarthritis, psoriasis, chronic inflammatory diseases (e.g., ulcerative colitis, Crohn's disease), hereditary diseases such as Osler-Weber Rendu disease and haemorrhagic teleangiectasia.

In an attempt to treat these diseases or conditions, many angiogenesis inhibitors have been discovered. Examples include endostatin (O'Reilly et al., 1997, Cell 88: 277), angiostatin (O'Reilly et al., 1994, Cell 79: 315), peptide CNGRCVSGCAGRC (SEQ ID NO: 3) (Arap et al., 1998, Science 279: 377), cyclic peptide RGDfV (Friedlander et al., 1995, Science 270: 1500), and monoclonal antibodies LM609 and P1F6 (Friedlander et al., 1995, Science 270: 1500). These drugs appear to target only on the angiogenesis aspect of the diseases without treating other additional, underlying mechanisms that are associated with or involved in the pathogenesis of the aforementioned diseases.

Therefore, a heretofore unaddressed need exists in the art to address the aforementioned deficiencies and inadequacies, especially in connection with the method of identifying drug candidates for treating cancer, inflammatory diseases, and/or angiogenesis-associated diseases.

SUMMARY OF THE INVENTION

One aspect of the invention relates to a pharmaceutical composition that contains a therapeutically effective amount of sCD26 and/or a biologically active derivative thereof, and a pharmaceutically acceptable carrier. The pharmaceutical composition may further contain a therapeutically effective amount of sFlt-1 and/or a biologically active derivative thereof.

Another aspect of the invention relates to a method of treating a disease which is associated with and/or progresses by a biological activity of an inflammatory cytokine. The method includes the step of administering to a mammalian subject, who would benefit therefrom, a pharmaceutical composition containing a therapeutically effective amount of sCD26 as described above.

In one embodiment of the invention, a pharmaceutical composition containing a therapeutically effective amount of sCD26 is administered to a mammalian subject having a disease associated with an increased interleukin activity, such as an increased IL-2 activity.

In another embodiment of the invention, a pharmaceutical composition containing a therapeutically effective amount of sCD26 is administered to a mammalian subject having a disease such as a tumor and/or an inflammatory disease. The inflammatory disease includes rheumatoid arthritis, macular degeneration, psoriasis, and diabetic retinopathy.

Yet in another embodiment of the invention, a pharmaceutical composition containing a therapeutically effective amount of sCD26 is administered to a mammalian subject having a disease such as a solid tumor, a tumor progression, tumor metastasis, and a latent tumor in a prevascular phase.

Another aspect of the invention relates to a method of treating a disease which is associated with and/or progresses by VEGF-associated angiogenesis and inflammatory cytokine-associated inflammation. The method includes the step of administering to a mammalian subject, who would benefit therefrom, a pharmaceutical composition containing therapeutically effective amounts of sCD26 and sFlt-1, and a pharmaceutically acceptable carrier.

In one embodiment of the invention, a pharmaceutical composition containing therapeutically effective amounts of sCD26 and sFlt-1 is administered to a mammalian subject having a disease such as a tumor and an inflammatory disease. Examples of an inflammatory disease include rheumatoid arthritis, macular degeneration, psoriasis, and diabetic retinopathy.

In another embodiment of the invention, a pharmaceutical composition containing therapeutically effective amounts of sCD26 and sFlt-1 is administered to a mammalian subject having a disease such as a solid tumor, tumor progression, tumor metastasis, and latent tumor in a prevascular phase.

Another aspect of the invention relates to a method of treating a disease in which the morbid state progresses by a biological activity of an inflammatory cytokine. The method includes the step of administering to a mammalian subject, who would benefit therefrom, a pharmaceutical composition containing a therapeutically effective amount of sCD26.

In one embodiment of the invention, a pharmaceutical composition containing a therapeutically effective amount of sCD26 is administered to a mammalian subject having a disease such as a tumor and an inflammatory disease. The inflammatory disease includes rheumatoid arthritis, macular degeneration, psoriasis, and diabetic retinopathy. The tumor may be a solid tumor, tumor progression, tumor metastasis, and latent tumor in a prevascular phase.

In another embodiment of the invention, a pharmaceutical composition containing a therapeutically effective amount of sCD26 is administered to a mammalian subject having a disease associated with an increased interleukin activity, such as an increased IL-2 activity.

Another aspect of the invention relates to a method of treating a disease in which the morbid state progresses by VEGF-associated angiogenesis and an inflammatory cytokine-associated inflammation. The method includes the step of administering to a mammalian subject, who would benefit therefrom, a pharmaceutical composition containing a therapeutically effective amount of sCD26 and sFlt-1, and a pharmaceutically acceptable carrier.

In one embodiment of the invention, a pharmaceutical composition containing therapeutically effective amounts of sCD26 and sFlt-1 is administered to a mammalian subject having a disease such as a tumor and an inflammatory disease. Examples of the inflammatory disease include rheumatoid arthritis, macular degeneration, psoriasis, and diabetic retinopathy.

In one embodiment of the invention, a pharmaceutical composition containing therapeutically effective amounts of sCD26 and sFlt-1 is administered to a mammalian subject having a disease such as a solid tumor, a tumor progression, tumor metastasis, and a latent tumor in a prevascular phase.

Yet another aspect of the invention relates to a method of inhibiting a biological activity of an inflammatory cytokine on a cell. The method includes the step of providing the cell with a pharmaceutical composition containing a therapeutically effective amount of sCD26, and a pharmaceutically acceptable carrier. The cytokine contains a motif XP, in which X is an amino acid and P is proline.

In one embodiment of the invention, a pharmaceutical composition containing a therapeutically effective amount of sCD26 is provided to a cell for inhibiting a biological activity of IL-2 on the cell.

In another embodiment of the invention, a pharmaceutical composition containing a therapeutically effective amount of sCD26 is provided to a cell present in a mammalian subject, who would benefit from an inhibition of a biological activity of an inflammatory cytokine on the cell. The subject is suffering from a disease associated with and/or progresses by a biological activity of an inflammatory cytokine. Examples of such diseases include a tumor and an inflammatory disease. The inflammatory disease includes rheumatoid arthritis, macular degeneration, psoriasis, and diabetic retinopathy. The disease tumor includes a solid tumor, tumor progression, tumor metastasis, and latent tumor in a prevascular phase.

Further another aspect of the invention relates to a method of inhibiting VEGF-associated angiogenesis and an inflammatory cytokine-associated inflammation. The method includes the step of administering to a mammalian subject, who would benefit therefrom, a pharmaceutical composition containing therapeutically effective amounts of sCD26 and sFlt-1.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 6 illustrates IL-2 activity in stimulating CTLL-2 cell proliferation was abolished by pre-treatment with sCD26. The cell line CTLL-2 was cultured in a medium containing IL-2 (lane 1), without IL-2 (lane 2), or containing sCD26-pretreated IL-2 (lane 3).

DETAILED DESCRIPTION OF THE INVENTION

Definitions

Figure 1:
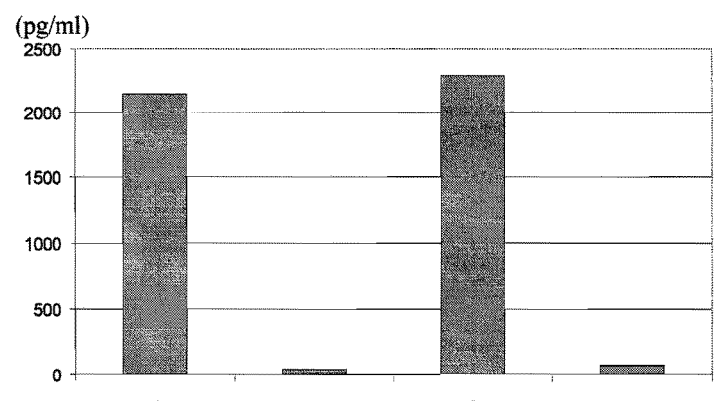
FIG. 1 illustrates the effect of trophoblast co-culture, or trophoblast culture supernatant, on the detection of VEGF produced by decidual leukocytes. Lane 1: leukocytes alone; Lane 2: leukocytes+trophoblasts; lane 3: leukocytes+JEG; lane 4: Leukocytes+trophoblasts supernatant.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "VEGFR1," "sVEGFR1," or "sFlt-1" refers to protein, peptide, or polypeptide receptor, an alternatively spliced form, or a biologically active derivative thereof, having vascular endothelial growth factor receptor type 1 (Flt) activity, for example, having the ability to bind a vascular endothelial growth factor. The biological activity of a sFlt-1 polypeptide may be assayed using any standard method, for example, by assaying sFlt-1 binding to VEGF. Soluble Flt-1 lacks the transmembrane domain and the cytoplasmic tyrosine kinase domain of the Flt-1 receptor. Soluble Flt-1 can bind to VEGF and P1GF with high affinity, but it cannot induce proliferation or angiogenesis and is therefore functionally different from the Flt-1 and KDR receptors. As used herein, sFlt-1 includes any sFlt-1 family member or isoform. Soluble Flt-1 can also mean degradation products or fragments that result from enzymatic cleavage of the Flt-1 receptor and that maintain sFlt-1 biological activity. Soluble Flt-1 can be used to antagonize VEGF function.

As used herein, the term "biologically active derivative of sFlt-1" refers to a biological active protein or peptide fragment that comprises an amino acid sequence modified from the human sFlt-1.

As used herein, the term "human sFlt-1" refers to a biological active protein or peptide fragment that comprises an amino acid sequence of sFlt-1 of a human origin.

As used herein, the term "soluble CD26," or "sCD26" refers to a protein, peptide, an alternatively spliced form, or a biologically active derivative thereof, that has DPPIV enzymatic activity. A soluble form of CD26 is capable of cleaving N-terminal dipeptides from polypeptides with either proline or alanine residues in the penultimate position. The enzymatic activity of sCD26 is usually assayed by digestion of a commercially available chemically synthesized substrate Gly-Pro-p-nitroanilide (Sigma, CAT NO G2901).

As used herein, the term "biologically active derivative of sCD26" refers to a biological active protein or peptide fragment that comprises an amino acid sequence modified from the human sCD26.

As used herein, the term "human sCD26" refers to a biological active protein or peptide fragment that comprises an amino acid sequence of sCD26 of a human origin.

As used herein, the term "neutralization of VEGF" refers to the blocking of VEGF from binding to its receptor and result in a loss of VEGF activity such as VEGF-dependent cell proliferation.

As used herein, the term "a mammalian subject" includes a mammalian animal and a human being.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are light or wrong, should limit the scope of the invention so long as the invention is practiced according to the invention without regard for any particular theory or scheme of action.

Material and Methods

Tissue samples were obtained from elective termination of first trimester pregnancies from Addenbrookes Hospital, Cambridge, UK.

Isolation of Decidual Leukocytes

Preparation of maternal decidual leukocytes was carried out as described by King et al. (Hum. Immunol., 24 (3); 195-205 (1989)) with minor modifications. Samples of decidual tissues were sorted by macroscopical examination and washed in cold RPMI 1640 (Invitrogen, USA, Catalog No. 21875-034) for 10-20 minutes before being minced into small pieces with a surgical blade. Approximately 10 grams of minced tissue were digested in 25 ml of RPMI 1640 containing 10% fetal calf serum (FCS) (Harlan Sera-Lab, UK, Catalog No. S-0001A), 2 ml of Collagenase (10 μg/ml, Sigma, U.S., Catalog No. C5138), and 0.5 ml DNase I (3 μg/ml, Sigma D5025) at 37° C. on a roller incubator for 30 minutes. The sample tube was centrifuged briefly to pellet pieces of tissue and the cell-containing supernatant was filtered through a 100 μm filter (Becton Dickinson, USA, Catalog No. 352360). The flow-through was centrifuged at 650×g for 5 minutes to pellet cells. The supernatant was added back to the tissue which had been passed through a 10 ml pipette a few times to further break up the tissue. The mixture was incubated for another 10 minutes at 37° C. The sample tube was then centrifuged briefly to pellet tissues and supernatant was filtered through 100 μm filter. Filtered supernatant was centrifuged at 650×g for 5 minutes to pellet the cells. The cell pellet was resuspended in 15 ml of PBS (Current Protocols in Molecular Biology, Wiley Press, page 4.2.3, 1996) containing 2% FCS and 0.1% azide before being overlaid onto 15 ml of LYMPHOPREP™, a ready-made, sterile and endotoxin-tested solution suitable for the purification of human mononuclear cells (Axis-Shield Diagnostics, Norway, Catalog No. 1114545). The tube was centrifuged at 710×g for 20 minutes without brake and the cells at the interface were collected and washed once in RPMI 1640 (10% FCS). Decidual leukocytes prepared in this method consisted of approximately 60% NK cells ($CD56^+$ $CD16^-$), 15-20% macrophages ($CD14^+$), 10% T cells and other stromal cells.

Isolation of Fetal Trophoblast Cells

Fragments of placental tissue were identified macroscopically and washed in RPMI 1640 medium for a few minutes. The tissue was scraped with a scalpel blade and then digested in 20 ml of prewarmed (37° C.) 0.25% trypsin (Becton Dickinson, USA, Catalog No. 215240) solution containing 0.02% EDTA for 8-9 minutes on a hotplate with stirring. Twenty milliliters of HAMS F12 (LIFE Technologies, USA, Catalog No. 074-90587) (20% NCS (Invitrogen, USA, Catalog No. 16010-167)) were added to the solution to stop trypsinization. The solution was then filtered through gauze and centrifuged in 50 ml tubes at 450×g to pellet the cells. The cell pellet was resuspended in 10 ml of HAMS F12 and the cell solution was overlaid onto 10 ml of LYMPHOPREP™, a ready-made, sterile and endotoxin tested solution suitable for the purification of human mononuclear cells (Axis-Shield Diagnostics, Norway, Catalog No. 1114545), and centrifuged at 710×g for 20 minutes. Cells at the interface were recovered and washed once with 10 ml of HAMS medium. To deplete placental macrophages, the cell pellet was resuspended in 3 ml of HAMS and seeded onto a petri dish and incubated for 20 minutes at 37° C. Fetal trophoblast cells in the supernatant were recovered by centrifugation at 600×g for 5 minutes.

Concentration of Fetal Trophoblast Cell Culture Supernatant

Fetal trophoblast cells isolated as described above were cultured in RPMI-1640 medium plus 10% fetal calf serum (FCS) at $1\times10^6$ cells/nil at 37° C. overnight. The supernatant was collected and centrifuged at 1,000×g for 5 minutes to pellet the cell debris before being loaded onto a centrifugal filter device CENTRICON® (Millipore, YM-10) and centrifuged at 2,000 RPM for around 1 hour. The volume was usually reduced to 1:10 of the original volume to obtain a 10×-concentrated supernatant.

EXAMPLE 1

Placental Trophoblast Co-Culture Inhibited the Detection of VEGF Secreted by Decidual Leukocytes Decidual Leukocytes Co-Cultured with Placental Trophoblasts Decidual leukocytes and placental trophoblasts were isolated as described above. A trophoblast tumor cell line JEG cultured in RPMI-1640 medium (10% FCS) was used as a negative control. One hundred μl of leukocytes ($3\times10^6$ cells/ml) were seeded onto each well of a 96-well U-bottom plate with or without 100 μl of the isolated trophoblasts, or with negative control cells JEG ($1\times10^6$ cells/ml). After overnight incubation, the culture supernatants were harvested and stored at −70° C. for later ELISA assay. One hundred μl of each stored supernatant was thawed and used in a VEGF ELISA assay (R&D, USA, Catalog No. DY293) according to the manufacturer's instruction manual.

FIG. 1 shows the results of the assay: Lane 1 shows the concentration of VEGF produced by decidual leukocytes and detected in the culture supernatant by the VEGF ELISA assay. Lane 2 shows the disappearance of the VEGF in the culture supernatant when the decidual leukocytes were co-cultured with isolated trophoblasts un the same dish. As a negative control, lane 3 illustrates the presence of VEGF when decidual leukocytes were co-cultured with the cell line JEG. The data indicates that the inhibition of VEGF detection was not an artifact induced by co-culture per se because JEG co-culture did not produce the same effect. Instead, it was specifically due to the co-culture with the isolated trophoblasts. This effect of trophoblasts on the detection of VEGF could also be repeated by adding the culture supernatant from trophoblast-only cell culture. The assay results indicated that it was possible that some kind of soluble factor(s) was secreted into the culture supernatant by trophoblasts and caused abolishment of VEGF detection in the ELISA assay.

EXAMPLE 2

Detection of Placental Soluble Fins-Like Tyrosine Kinase 1 (sFlt1) in Supernatant of Trophoblast Cell Culture It has been know that sFlt-1, which was initially purified from human umbilical endothelial cells, is produced by trophoblast cells in vivo. In one example, specific metalloproteinases released from the placenta may cleave the extracellular domain of Flt-1 receptor to release the N-terminal portion of Flt-1 into circulation. A soluble form of Flt-1 (i.e., sFlt-1) can be detected in peripheral blood and is a ligand with a high affinity to VEGF. To investigate whether sFlt-1 was a factor secreted into the culture supernatant by trophoblast co-culture and caused abolishment of VEGF detection in FIG. 1, the following experiments were performed.

Western Blot Analysis

Twenty microliters of trophoblast supernatant or pure sFlt-1 (R&D Systems CAT NO 321-FL) were mixed with 4 μl of 6×SDS gel loading dye, and boiled for 5 minutes before being loaded onto a 10% SDS polyacrylamide gel (Bio-Rad CAT NO 161-1101). The gel was run at 100 volts for 1.5 hours and blotted onto a PVDF membrane at 100 volts for 1 hour. The blot was incubated in a 10% milk/TBST buffer containing 0.1 μg/ml polyclonal goat anti-sFlt-1 antibody (R&D Systems CAT NO AF321) for 2 hours at room temperature. After washing 3 times in the TBST buffer, a secondary antibody rabbit anti-goat HRP-conjugated antibody (DakoCytomation CAT NO P0449) was used in the blot at dilution 1:2000 in 10% milk/TBST for 1 hour. After washing 3 times, the band was detected using an ECL kit (GE Healthcare CAT NO RPN2106) according to the manufacturer's instruction manual.

Figures 2A, 2B:
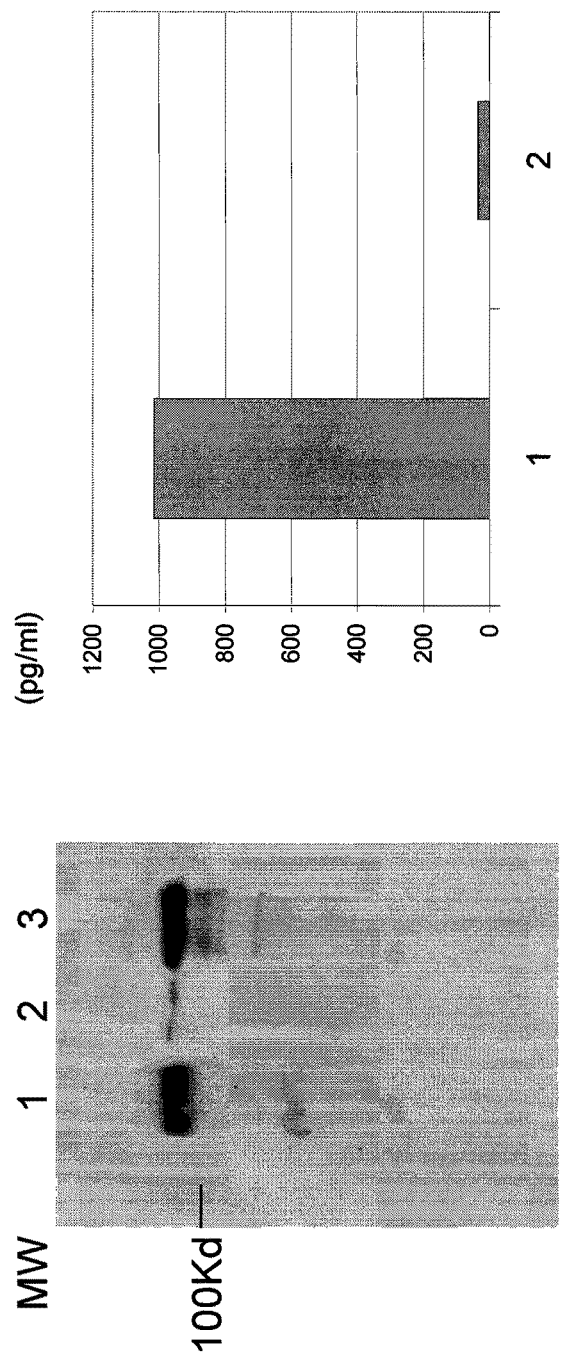
FIG. 2A illustrates the result of the Western blot analysis of the supernatant of trophoblast culture as detected by an antibody specific against sFlt-1. Lane 1: supernatant of trophoblast culture; lane 2: 1 ng sFlt-1; lane 3: 10 ng sFlt-1.
FIG. 2B illustrates the result of the ELISA detections of sFlt-1 in the supernatant of the trophoblast cell culture. Lane 1: supernatant of trophoblast culture; lane 2: culture medium only.

FIG. 2A is a Western blot that shows using an anti-sFlt-1 antibody, a protein band of around 110 Kd was detected in the trophoblast supernatant (Lane 1). The same molecular weight band was detected in the positive control as well (lanes 2 and 3, loaded with different amount of pure sFlt-1 protein, respectively). The result indicates soluble Flt-1 was present in the trophoblast supernatant.

Soluble Flt-1 ELISA Assay

One hundred microliters of the supernatant from the trophoblast cell culture were used for assay of soluble Flt-1 present in the trophoblast culture by using sFlt-1 ELISA kit (R&D Systems, CAT NO DVR100B) according to the manufacturer's instruction manual. FIG. 2 B shows the result of the ELISA detections of sFlt-1 in the supernatant of the trophoblast cell culture. Lane 1: supernatant of trophoblast culture; lane 2: culture medium only. The result indicated that a large amount of soluble Flt-1 was detected in the supernatant of trophoblast culture by ELISA.

EXAMPLE 3

Neutralization of VEGF by sFlt-1

VEGF ELISA Assay

Figures 3A, 3B:
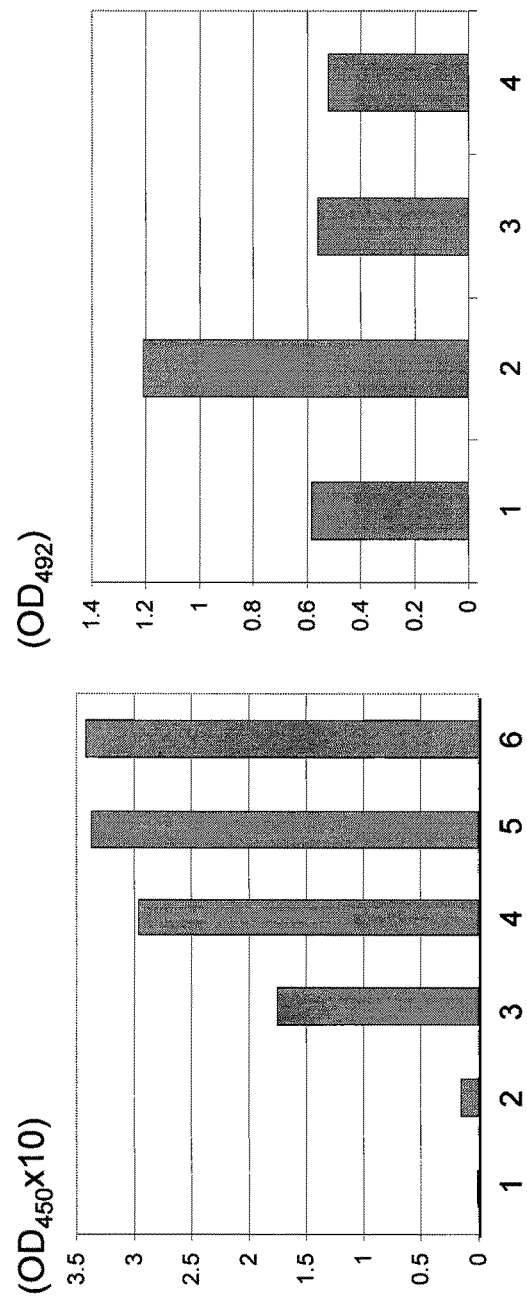
FIG. 3A illustrates the detected concentrations of VEGF after incubation with various amounts of sFlt-1 in the VEGF ELISA assay. The amount of sFlt-1 used for incubation with VEGF was 10, 3, 1, 0.3, 0.1, and 0 ng in lanes 1~6, respectively.
FIG. 3B illustrates VEGF-dependent proliferation of HUVECs was abolished by pre-treatment of VEGF with sFlt-1. HUVECs were cultured in basal medium alone (lane 1), medium containing VEGF (lane 2), medium containing sFlt-1 treated VEGF (lane 3), or medium containing anti-VEGF antibody-treated VEGF (control, lane 4).

Pure sFlt-1 (1 μg/ml) was serially diluted (dilution 1:3) in PBS buffer. Ten microliteres of each diluted sFlt-1 were mixed with 90 μl of VEGF (1.1 ng/ml; R&D Systems, MN, USA) and incubated for 1 hour at 37° C. After the incubation, the 100 μl mixture was used for VEGF ELISA. FIG. 3A shows the detected concentrations of VEGF after incubation with various amounts of sFlt-1 in the VEGF ELISA assay. The amount of sFlt-1 used for incubation with VEGF was 10, 3, 1, 0.3, 0.1, and 0 ng in lanes 1-6, respectively. Since soluble Flt-1 was serially diluted from 10 ng down to 0.1 ng before incubation with 1 ng of VEGF, the result indicates that sFlt-1, in a sufficient concentration, binds to all the VEGF and prevents VEGF from being detected in ELISA assay. The neutralization of VEGF by sFlt-1 was dose-dependent. When 3 ng of sFlt-1 was used, almost all of 1 ng of VEGF in the solution was neutralized (lane 2).

EXAMPLE 4

Soluble Flt-1 Abolished VEGF-Dependent HUVECs Proliferation

Isolation of Human Umbilical Vein Endothelial Cells (HUVECs)

HUVECs were isolated as described by Jaffe, E. A. et al. (J. Clin. Invest. 52 (11): 2745-2756, 1973) with minor modifications. Briefly, human umbilical cord was collected into 150 ml of PBS buffer containing 1 μg/ml fungizone (Gibco, USA, Cat No. 15295-017). The cord was washed with sterile PBS and the damaged ends were cut off with a surgical blade. The vein was located and cannulated with a sterile Kwill filling tube (Avon Medicals, UK, Cat No. E910) at both ends of the cord. The umbilical cord was tied up at the cannulated region with a sterile thread. The cord blood was then flushed out with 100 ml PBS, and 20 ml of PBS was gently flushed back and forth between two 20 ml syringes (Becton Dickinson, USA, Catalog No. 300613). After flushing the cord thoroughly, the excess PBS was removed. Ten milliliters of collagenase solution (10 μg/ml) were added at (Sigma, USA, Catalog No. C-9891) and the ends of cannulas were plugged. The cord was then placed in a pre-warmed beaker containing PBS for 10 minutes. The collagenase solution in the cord was gently flushed back and forth between two syringes and the flow-through was collected in a 50 ml centrifuge tube. The cord was then washed with 10 ml of Medium-199 medium (Sigma, USA, Catalog No. M-7528) into the same tube. The tube was centrifuged at 200×g for 5 minutes to collect the HUVECs. The cells were re-suspended in 10 ml of endothelial cell growth medium (PromoCell, USA, Catalog No. C22010) and cultured in an incubator at 37° C. for further experiments.

Effect of sFlt-1 on VEGF-Dependent HUVEC Proliferation

HUVECs isolated as described above were re-suspended in Medium-199 (Sigma, USA, Catalog No. M-7528) at $2 \times 10^5$ cells/ml, and plated 50 μl per well in a 96-well flat bottom plate (Becton Dickinson, USA, Catalog No. 353072). VEGF was diluted in Medium-199 medium to give 1 μg/ml. Neutralization of VEGF by sFlt-1 was accomplished by incubating VEGF (1 μg/ml) with equal volume of sFlt-1 (5 μg/ml; R&D Systems, MN, USA) at 37° C. for one hour. After the neutralization, the VEGF in the solution was diluted to 20 ng/ml with an assay medium (M-199 plus 10% FCS and 10 mM HEPES). The sFlt-1 pre-treated and diluted VEGF was added into the HUVEC culture at 50 μl per well. As control, VEGF (1 μg/ml) was incubated with anti-VEGF antibody (R&D MAB293, 10 μg/ml) at room temperature for one hour. After addition of control VEGF or sFlt-1 pre-treated VEGF into the HUVECs culture, the plate was incubated at 37° C. for three days before measuring cell proliferation by using a tetrazolium based assay kit (Promega CAT No G3580).

The proliferation of HUVECs reflects a response to the stimulation by VEGF. Without the supply of VEGF, HUVEC culture will stop growing and gradually die off. Since HUVEC proliferation in response to VEGF stimulation is essential in angiogenesis in vivo, a test compound or composition that results in an inhibition of VEGF activity in the present assay may be considered to have anti-angiogenesis properties.

As shown in FIG. 3B, HUVECs cultured in a medium containing VEGF (lane 2) exhibited an increase in cell growth as compared to those cultured in a basic medium without VEGF (lane 1). The result indicated that VEGF present in the culture medium stimulated proliferation of HUVECs. HUVECs cultured in a medium containing sFlt-1 pre-treated VEGF (i.e., neutralized VEGF), however, did not exhibit an increase in cell growth. This indicated VEGF had lost activity in stimulating HUVECs proliferation due to neutralization by pre-treatment with sFlt-1 before being added into the HUVECs culture. Since HUVEC proliferation in response to VEGF stimulation is essential in angiogenesis, sFlt-1, by inhibiting or abolishing VEGF activity in stimulating HUVECs proliferation, has proved to possess anti-angiogenesis property.

EXAMPLE 5

Placental sCD26 Identified in the Supernatant of Trophoblast Culture

Figure 4:
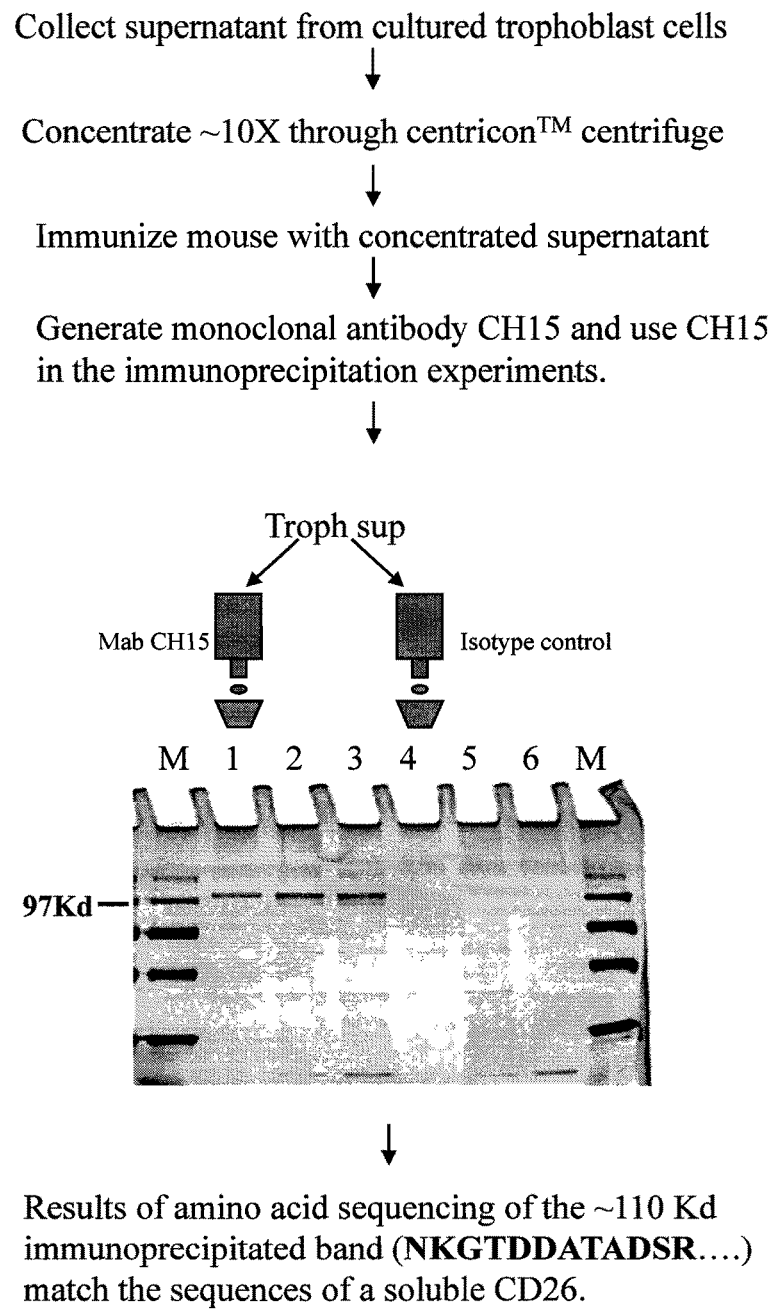
FIG. 4 illustrates the steps for identifying the presence of placental sCD26 in the supernatant of trophoblast culture.

FIG. 4 illustrates the steps of generating monoclonal antibody CH15 and using the generated CH15 in the immunoprecipitation experiments.

Generation of Hybridoma Cell lines Producing Monoclonal Antibodies Against Proteins in the Supernatant from Trophoblasts Culture Ten times concentrated supernatant from trophoblast culture prepared as described above was used to immunize a Balb/c mouse. The spleen cells from the immunized mouse were fused with SP2/0 cells according to the manufacturer's procedure for generation of hybridoma (StemCell Technologies, CLONACELL™-HY, Catalog No. 03800). A hybridoma cell clone producing IgG antibody CH15 was identified.

Purification of Monoclonal Antibody CH15 from Hybridoma Supernatant

The monoclonal antibody CH15 in the hybridoma cells culture supernatant was purified by protein-A column. Briefly, 0.5 g protein-A sepharose powder (Sigma, USA, Catalog No. P3391) was hydrated in 1 ml PBS buffer (pH 7.4) and loaded into a plastic column (Bio-Rad, USA, Catalog No. 732-1010). The column was washed with 10 ml PBS buffer (pH 8). The hybridoma supernatant was then passed through the protein-A column slowly allowing the antibody to bind to the protein-A column. Afterwards, the protein-A column was washed a few times with the buffer solution and antibody eluted from the column with 100 mM glycine (pH 3) (Antibodies, Harlow, E. and Lane, D., Cold Springs Harbor Lab Press, 1988, p. 310).

Immobilization of CH15 onto Agarose Gel

The purified monoclonal antibody CH 15 (200 µg) as aforementioned was immobilized onto an agarose gel for immunoprecipitation according the manufacturer's instruction manual (SEIZE™ primary immunoprecipitation kit, Pierce Catalog No. 45335). FIG. 4 illustrates Monoclonal antibody CH15 (Mab CH15, next to the column) was immobilized onto the column.

Immunoprecipitation of CH15-Specific Protein in Trophoblast Culture Supernatant

As shown in FIG. 4, ten times concentrated trophoblast supernatant (abbreviated as Troph sup in FIG. 4) was loaded into the column and incubated with the CH15 antibody-conjugated agarose gel described above for overnight at 4° C. to allow the CH15 antibody to bind the CH15-specific factor in the supernatant. The agarose gel was then washed a few times with a buffer solution and the proteins were eluted from the antibody-conjugated agarose gel with an elution buffer.

Visualization of CH15-Immunoprecipitated Protein on a Polyacrylamide Gel

The aforementioned, eluted sample (20 µl) was mixed with a gel loading dye (5 µl) and boiled for 5 minutes. The sample was then loaded into a 10% SDS polyacrylamide (SDS-PAGE) gel and electrophoresis was run at 100 volts for 1.5 hours in Tris-Glycine buffer (Current Protocols in Molecular Biology, Wiley Press, page A.2.5, 1996) with 2 mM mercaptoacetic acid (Sigma, USA, Catalog No. T-6750). After the gel electrophoresis, the proteins in the gel were blotted to a PVDF membrane (Bio-Rad, USA, Catalog No. 162-0185) in CAPS buffer (19 mM CAPS (Sigma, USA, Catalog No. C-4142), 5 mM DTT (Sigma, USA, Cat No. D9163), 10% Methanol, (pH 11) at 50 volts for one hour. After blotting, the membrane was stained with Coomassie Blue R-250 (Bio-Rad, USA, Catalog No. 161-0435) or stained by silver staining (Bio-Rad, USA, Catalog No. 161-0449) according to the manufacturer's instructions to visualize the proteins immunoprecipitated by CH15.

FIG. 4 illustrates the protein bands visualized by silver staining. Lanes 1~3 are eluted fractions from the antibody-conjugated agarose gel. Lanes 4~6 are eluted fractions from a negative control. After staining, a protein band of approximately 110 kDa (lanes 1-3, located slightly above the 97 Kd marker band) was cut out and sequenced. The results of amino acid sequencing of the ~110 Kd immunoprecipitated band (NKGTDDATADSR . . . ) (SEQ ID NO: 1) matched the sequence of sCD26.

Identification of Placental sCD26 Present in Trophoblast Culture Supernatant

The amino acid sequencing data indicates that the immunoprecipitated protein was a soluble form of placental CD26. The results indicated that placental sCD26 was present in the supernatant of cultured trophoblast cells and immunoprecipitated by CH15 on the SDS PAGE gel.

The above disclosures illustrate how to obtain and identify one form of sCD26 from the human placenta trophoblast cells. Different forms of soluble CD26 have also been reported. For example, sCD26 that is found in the normal human blood has an amino acid sequence that is ten residues shorter than its placenta counterpart. Soluble CD26 in a recombinant protein form may be obtained from commercial sources such as R&D Systems (Minneapolis, U.S.A.).

Human blood CD26 is a 240 kDa homodimeric type II membrane glycoprotein comprised of two 120 kDa subunits. (Mentlein, R., International Review of Cytology, 235: 165-213, 2004). It is also known as a dipeptidyl peptidase IV (DPPIV). As a membrane-bound glycoprotein, it possess various functional properties including modulating the activity of various biologically important peptides (Dang et al., Histol. Histopathol., 17: 1213-1226, 2002). CD26 has been found expressed on a variety of cell types, particularly melanocytes, epithelial cells, endothelial cells and lymphocytes.

Human blood sCD26, which lacks the first 38 residues as compared to its counterpart membrane bound CD26, has been postulated as a cleaved product from the membrane CD26. (Iwaki-Egawa et al., J. Biochem. (Tokyo) 124; 428-433 (1998)).

Figures 5A, 5B:
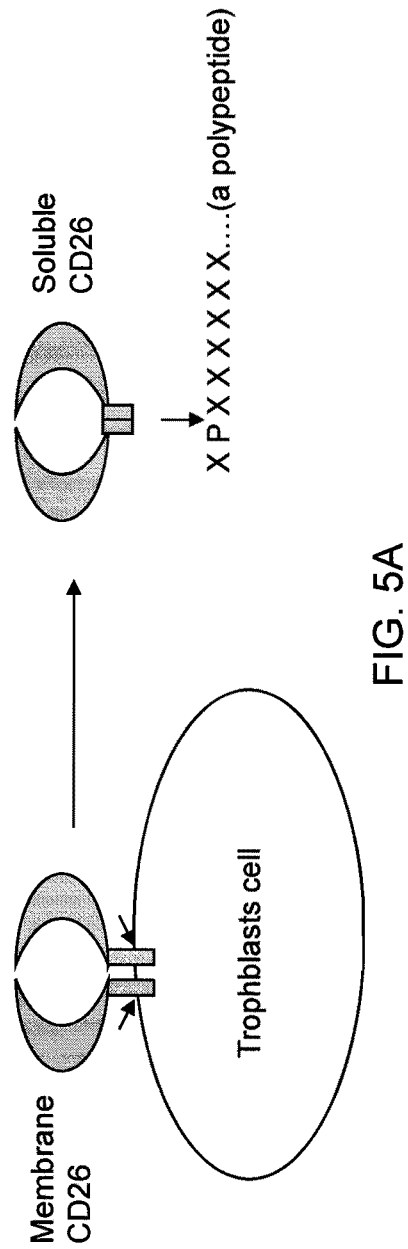
FIG. 5A is a schematic representation illustrating membrane bound CD26 and soluble CD26, and the recognition of the XP motif by soluble CD26.
FIG. 5B illustrates IL-2 contains the motif XP.

Human placental sCD26, a cleaved product from the placental membrane CD26 as well, lacks the first 28 residues as compared to the placenta membrane bound CD26. Therefore, a human placental sCD26 has an additional 10 amino acid residues at its N-terminus as compared to human blood sCD26. FIG. 5A illustrates a placental membrane CD26 as a homodimeric, membrane-bound protein, which may be cleaved (indicated by two arrows) and result in a homodimeric, placental sCD26.

A survey of literature led to the finding that sCD26 has been reported to cleave a $NH_2$-terminal dipeptide in a polypeptide having either L-proline or L-alanine at the penultimate position (Fleischer, Immunol Today 15; 180-184 (1994)). Many biologically active polypeptides have this sequence. For example, a proline residue is present at the penultimate position in many cytokines, such as IL-1β, IL-2, IL-6, and G-CSF. (Ansorge et al., Biomed Biochim Acta 50; 799-807 (1991)). FIG. 5A illustrates sCD26 cleaves an amino-terminal dipeptide in a polypeptide that has a L-proline at the penultimate position.

Studies have shown that sCD26 has many physiological roles, including a role in immune regulation as a structure capable of transmitting T cell activation signals and a role as a regulator of biological processes through its cleavage of biological factors. Activation of a T cell is a complex process involving various secreted interleukins, which acts as local chemical mediators. Activation is thought to begin when the T cell, by unknown means, is stimulated by the antigen-presenting cell to secrete one or more interleukins. Interleukin 2 (IL-2) is a protein produced by T-lymphocytes that have been activated by an antigen. IL-2 stimulates other lymphocytes to activate and differentiate. IL-2 is a central cytokine required for the activation of T, B and natural-killer (NK) cells. (Tenbrock et al., Int Rev Immunol., 23 (3-4); 333-345, 2004).

Human IL-2 is a protein of 133 amino acids (15.4 kDa) with a slightly basic pI that does not display sequence homology to any other factors. Murine and human IL-2 display a homology of approximately 65%. IL-2 is synthesized as a precursor protein of 153 amino acids with the first 20 amino-terminal amino acids functioning as a hydrophobic secretory signal sequence. The protein contains a single disulfide bond at positions Cys58 and Cys105, which is essential for biological activity.

It is well known in the art that IL-2 is a pro-inflammation cytokine in the human immune system. There are numerous examples of the pathological role IL-2 plays in the inflammatory and immune diseases. For example, the level of IL-2 production is altered in patients suffering from the multiple sclerosis and reduced in patients suffering from systemic lupus erythematosus. (Dejica D., Rorum Arch Microbiol Immunol., 60 (3): 183-201, 2001; Herndon et al., Clin. Immunol., 103 (2), 145-53, 2002; Tenbrock et al., Int Rev Immunol., 23 (3-4): 333-45, 2004). Development of a molecule that is able to alter the IL-2 activity would be useful in the treatment of autoimmune and inflammatory disorders. Since many cytokines contains a proline residue at the penultimate position, the effects of placental sCD26 on IL-2 were further investigated and experiments were illustrated as follows.

EXAMPLE 6 sCD26 Abolished IL-2 Activity in Stimulating CTLL-2 Cell Proliferation

Purification of Placenta Soluble CD26

For every gram of PBS-washed placenta tissue, four milliliters of RPMI-1640 (w/o FCS) were added and the tissue was incubated at 37° C. incubator for 3-4 days before supernatant was harvested. Supernatant was centrifuged at 700×g for 5 minutes to remove debris. The soluble CD26 in the solution was purified through ADA (Sigma CAT NO A6648) column according to the published method (de Meester et al J Immunol Methods. 1996 Jan. 16; 189 (1): 99-105). The purified sCD26 was eluted from the column with 30 ml of 2 mM Tris (pH8) and concentrated down to 3 ml using Centricon Plus-70 device (Amicon CAT NO UFC 701008) and aliquots stored at 4° C. for later use. The purified and concentrated sCD26 was used later for the following experiment.

Production of Human IL-2 with Native N-Terminus

Most of commercially available IL-2 is produced from bacteria and thus the N-terminus of the protein is modified with an extra amino acid Methionine (M) on it. The methionin-N-terminal IL-2 is not an ideal substrate for studying the function of soluble CD26 because sCD26 recognizes only the exact N-terminal amino acid sequences of a protein. We therefore cloned the human IL-2 gene into a plasmid vector with a Flag-tag at the C-terminus for later purification purposes, and transfected the recombinant vector into a Eucaryotic cell line BaF3. A stable clone that produced IL-2 was identified and grown to a large volume. The IL-2 was produced and concentrated in the supernatant, which was then used in the following experiment.

CTLL-2 Cell Proliferation Assay

The CTLL-2 (ATCC, TIB214) cell line constitutively expresses IL-2 receptors and depends entirely on the presence of exogenous IL-2 for cell growth. The CTLL-2 cells were used to assay the effect of sCD26 on the activity of IL-2 in stimulating CTLL-2 cell growth. The activity of IL-2 in stimulating CTLL-2 cell growth was assayed by using a cell proliferation kit for measuring the absorbance at $OD_{490}$. Before the experiment, CTLL-2 cells ($0.1 \times 10^6$ cells/ml) were washed twice with RPMI-1640 and plated 50 μl per well in 96-well plates. The IL-2, which was produced as described above, was pre-treated with the sCD26, which was purified from placenta cell culture supernatant as mentioned above, by mixing 1 μl of concentrated IL-2 supernatant with 20 μl of purified, concentrated sCD26 for 1 hour at 37° C. After treatment, IL-2 was adjusted to 50 μl and mixed with CTLL-2 cells, $0.1 \times 10^6$/ml at 50 μl per well. The cell culture was incubated at 37° C. for 3 days before measuring cell proliferation at $OD_{490}$ (Promega, CAT No G3580).

FIG. 5A illustrates soluble CD26 can recognize a polypeptide that contains a motif XP and cleave the peptide bond thereafter. FIG. 5B illustrates IL-2 contains an amino acid sequence APTSSSTKK . . . (SEQ ID NO: 2) with the motif AP (alanine-proline) that can be recognized by sCD26.

FIG. 6 illustrates the growth of cell line CTLL-2 was dependent on IL-2 in the growth medium. Without the supply of exogenous IL-2, the CTLL-2 cell line stopped growth and died off quickly (lane 2) as compared to that in the medium containing IL-2 (lane 1). Pre-treatment of IL-2 with aforementioned purified and concentrated sCD26 rendered the IL-2 inactive as it lost the activity in stimulating CTLL-2 cell proliferation (FIG. 6, lane 3). Since IL-2 is a pro-inflammation cytokine in human immune system, soluble CD26 may be useful as an inflammation inhibitor through its inhibition on IL-2 activity.

EXAMPLE 7

Neutralization of VEGF by Sera from Pregnant Females

Figure 7:
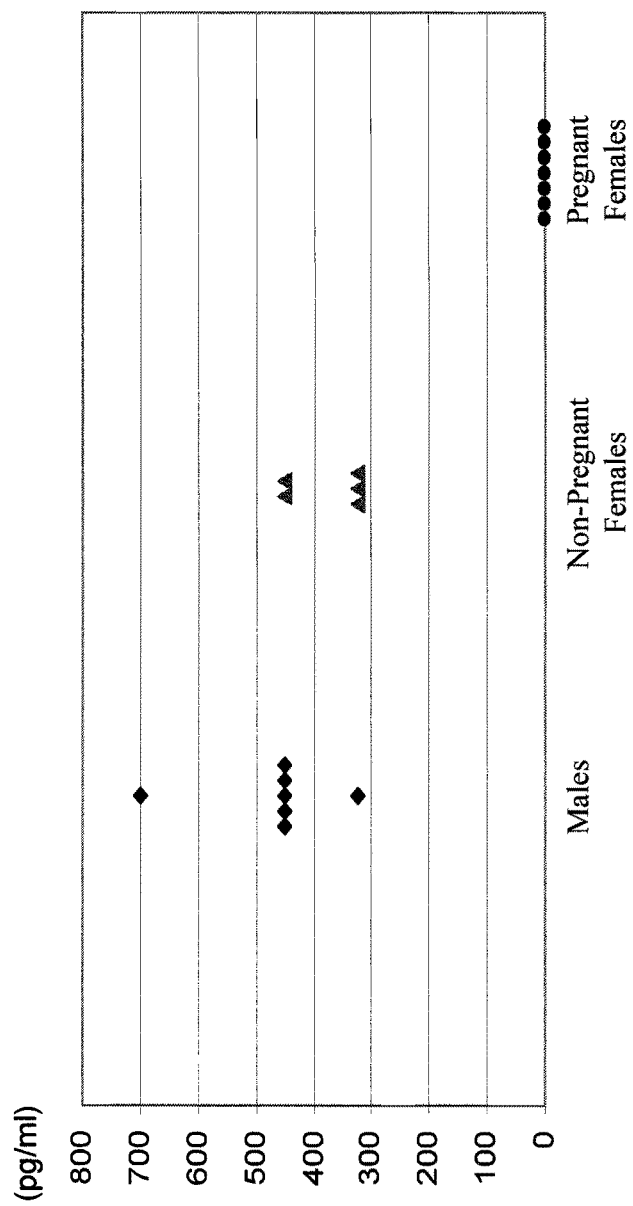
FIG. 7 illustrates neutralization of VEGF by sera from pregnant women in ELISA.

Sera from 7 pregnant women were collected as described previously. One hundred microliters of serum were incubated with 1 ng of VEGF at 37° C. for 2 hours before performing the VEGF ELISA assay (FIG. 7, group 3). Sera from 7 men and 5 non-pregnant women were also collected and used as controls in the same experiment (FIG. 7, groups 1 and 2, respectively). As shown in FIG. 7, only pregnant woman's serum prevented the detection of VEGF due to the presence of a soluble factor (i.e. sFlt-1).

EXAMPLE 8

Blood sFlt-1 Level Increases During Pregnancy

Measurement of Serum sFlt-1 Level

Ten milliliters of blood were taken from each volunteer blood donor. Blood was overlaid on 3 ml of Lymphoprep™ (Axis-Shield UK, CAT NO 1114545) and centrifuged for 20 minutes at 700×g. The top layer serum was harvested and aliquots were stored at −70° C. for the later ELISA assay. The amount of soluble Flt-1 in the serum was measured using sFlt-1 ELISA kit (R&D Systems CAT NO DVR100B) according to the manufacturer's instruction manual.

Figures 8A, 8B:
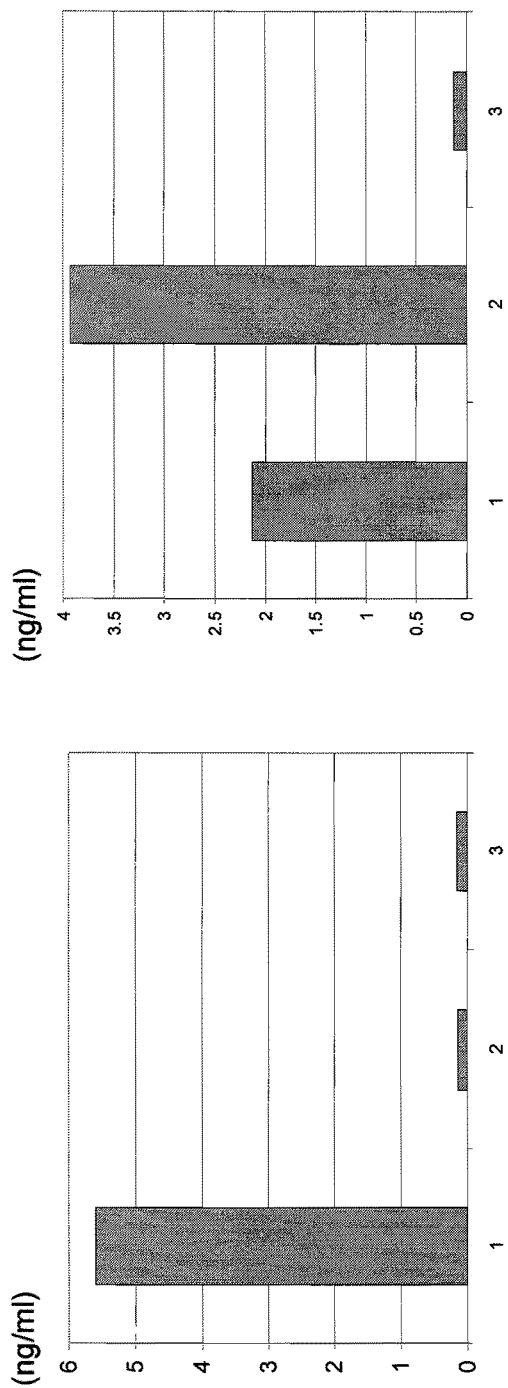
FIG. 8A illustrates the average amount of sFlt-1 from serum samples of 5 subjects in each test group: pregnant women (lane 1), non-pregnant women (lane 2) and men (lane 3).
FIG. 8B illustrates the level of sFlt-1 in the serum from a pregnant woman at 20 weeks of pregnancy (lane 1), 30 weeks of pregnancy (lane 2) and 10 weeks after giving birth (lane 3).

FIG. 8A illustrates the average amount of sFlt-1 from serum samples of 5 subjects. Lane 1: pregnant women; lane 2: non-pregnant women; lane 3: men. The results indicate that only significant amount of soluble Flt-1 could be detected in the serum of pregnant women (lane 1) as compared to that of non-pregnant women and men (lane 2 and 3).

FIG. 8B illustrates the level of sFlt-1 in the serum from a pregnant woman at 20 weeks of pregnancy (lane 1), 30 weeks of pregnancy (lane 2) and 10 weeks after giving birth (lane 3). The result indicates that the levels of soluble Flt-1 in the serum increased during the course of the pregnancy, but disappeared about 3 months after giving birth.

Angiogenesis has been implicated in progression of inflammatory arthritis, psoriasis, atherosclerosis as well as tumor growth and metastasis. Pathological angiogenesis is a hallmark of cancer and various ischaemic and inflammatory diseases. Angiogenesis is crucial for tumor growth and metastasis (Keith Dredge et al. Current Opinion in Investigational Drugs. 4 (6): 667-674, (2003)). New blood vessel development is an important process in tumor progression. It favors the transition from hyperplasia to neoplasia, i.e., the passage from a state of cellular multiplication to a state of uncontrolled proliferation characteristic of tumor cells. Neovascularization also influences the dissemination of cancer cells throughout the entire body eventually leading to metastasis formation. Ninety percent of all cancers are solid tumors and thus depend on angiogenesis to support their growth. It has also been shown that the resection of a primary tumor is often accompanied by metastases caused by a systemic disturbance of the angiogenic balance of the body. All these standard therapies could profit from a concomitant treatment that would restrict latent tumors in a prevascular phase.

It has been suggested inhibiting new blood vessel formation as a way to fight cancer. The malignant tissue would be deprived of its oxygen and nutrient supply, as well as be unable to eliminate metabolic wastes. This in turn would inhibit tumor progression and metastatic progression that accompanies most advanced cancers. There are five main steps of the angiogenic process that can be interrupted: (1) Inhibiting endogenous angiogenic factors, such as bFGF (basic Fibroblast Growth Factor) and VEGF (Vascular Endothelial Growth Factor); (2) Inhibiting degradative enzymes (Matrix Metalloproteinases) responsible for the degradation of the basement membrane of blood vessels; (3) Inhibiting endothelial cell proliferation; (4) Inhibiting endothelial cell migration; and (5) Inhibiting the activation and differentiation of endothelial cells.

Neutralization of VEGF has been used as a strategy for the treatment of cancer. For example, a new drug AVASTIN™, which is a monoclonal antibody, works by binding to and inhibiting the action of vascular endothelial growth factor (VEGF). VEGF is a substance that binds to its receptor on certain cells to stimulate new blood vessel formation. When VEGF is bound by AVASTIN™, it cannot stimulate the formation and growth of new blood vessels (angiogenesis). AVASTIN™ enhances the effects of chemotherapy, but does not appear to be very effective when given alone in patients with colorectal cancer.

The present invention discloses, among others, that soluble Flt-1 is capable of neutralizing VEGF. Since anti-VEGF or anti-angiogenesis has been proved to be useful in treating angiogenesis-dependent cancer, sFlt-1 by its VEGF-neutralizing activity may be useful for treating cancer or tumor of which the growth is dependent on angiogenesis.

Inflammation has also been implicated in Cancer. Chronic inflammation is associated with cancer development. Early and persistent inflammatory responses observed in or around developing neoplasms regulate many aspects of tumor development. (Leon C. L. et al. "Inflammation, proteases and cancer." European Journal of Cancer, Vol. 42, Issue 6, pages 728-734) Inflammation functions at all three stages of tumor development: initiation, progression and metastasis. Inflammation contributes to initiation by inducing the release of a variety of cytokines and chemokines that alert the vasculature to release inflammatory cells and factors into the tissue milieu, thereby causing oxidative damage, DNA mutations, and other changes in the microenvironment, making it more conducive to cell transformation, increased survival and proliferation. Moreover, there is a strong association between chronic inflammation and cancer. An appreciation of the importance of inflammation has already led to clinical trials of anti-inflammatory drugs (e.g., COX-2 inhibitors) for cancer prophylaxis and treatment. (National Cancer Institute, Division of Cancer Biology, "Executive Summary of Inflammation and Cancer Think Tank." [retrieved on 2007-11-17]. Retrieved from the Internet:<URL: http://dcb.nci.nagov/thinktank/Executive_Summary_of_Inflamma-tion_and_Cancer_Thi nk_Tank.cfm>)

Angiogenesis is also associated with inflammation or inflammatory disorders. Vascular endothelial growth factor (VEGF) has been shown to a have a central involvement in the angiogenic process in rheumatoid arthritis (RA). The additional activity of VEGF as a vascular permeability factor may also increase oedema and hence joint swelling in RA. Several studies have shown that targeting angiogenesis in animal models of arthritis ameliorates disease. (Paleolog E M. Arthritis Res. 2002; 4 Suppl 3:S81-90.) Since sFlt-1 has anti-angiogenesis/anti-VEGF activity, it may also be useful for reducing the degree of angiogenesis in inflammatory diseases including rheumatoid arthritis as well as in chronic inflammation which is associated with cancer.

It has been reported that pregnancy induces immunological alterations. A variety of hormonal and immunological alterations are induced by pregnancy in order to protect semi-allogenic fetus from rejection. Systemic effects of altered immunoregulation induced by pregnancy influence the activity of rheumatoid arthritis (RA) and other autoimmune disease. Pregnancy induces improvement or even remission of disease activity in 75% of RA patients. The increase of circulating inhibitors of proinflammatory cytokines occurring in pregnancy could act as a potent anti-inflammatory agent in joint inflammation. It is likely that neutralization of proinflammatory cytokines may be the key to remission. (Ostensn M, Villiger P M, "Immunology of Pregnancy-pregnancy as a remission inducing agent in rheumatoid arthritis." Transpl Immunol. 2002 May; 9(2-4): 155-60.)

The present invention describes, among others, soluble Flt-1 was detected in large amount only in pregnancy. Since VEGF is implicated in RA and sFlt-1 is capable of neutralizing VEGF, an increase in the levels of serum sFlt-1 in pregnancy is likely to be one of the factors that contribute a remission of RA during pregnancy. Moreover, sCD26 is produced by trophoblast cells, which may in turn neutralize inflammatory cytokines such as interleukins, thereby further contributing a remission of RA during pregnancy.

Soluble CD26/DPPIV has an essential role in immune regulation as a T cell activation molecule and a regulator of chemokine function. It has been suggested that sCD26 may exert its enhancing effect on T cell response to recall antigen via its effect on antigen-presenting cells. Studies have shown that sCD26 is transported into monocytes and upregulates the expression of CD86 on monocytes through its DPPIV activity, both at the protein and mRNA levels. It has been therefore suggested that sCD26, particularly its DPPIV enzymatic activity, enhance T cell immune response to recall antigens through its direct effect on antigen-presenting cells (Dang and Morimato, Histol Histopathol. 17: 1213-1226 (2002)). Clinical studies have shown that plasma levels of DPPIV/CD26 from rheumatoid arthritis patients were significantly decreased when compared to those from osteoarthritis patients (Nathalie Busso et al., American Journal of Pathology, Vol. 166, No. 2, 433-442 (2005)).

The present invention discloses, among others, that sCD26 is produced by trophoblast cells. Moreover, the invention discloses sCD26 is capable of inhibiting Interleukins, such as IL-2. Therefore, sCD26 may be useful for anti-inflammation in diseases including cancer, rheumatoid arthritis, and other inflammatory disorders, in addition its T-cell activation activities as aforementioned.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of treating rheumatoid arthritis, comprising administering to a subject in need thereof a pharmaceutical composition comprising:
   a) a therapeutically effective amount of unmodified soluble CD26;
   b) a therapeutically effective amount of unmodified soluble Flt-1; and
   c) a pharmaceutically acceptable carrier, wherein the unmodified soluble CD26 and the unmodified soluble Flt-1 are isolated from the subject species.

2. The method of claim 1, wherein the pharmaceutical composition consists essentially of:
   a) a therapeutically effective amount of unmodified soluble CD26;
   b) a therapeutically effective amount of unmodified soluble Flt-1; and
   c) a pharmaceutically acceptable carrier.

3. The method of claim 2, wherein the pharmaceutical composition consists of:
   a) a therapeutically effective amount of unmodified soluble CD26;
   b) a therapeutically effective amount of unmodified soluble Flt-1; and
   c) a pharmaceutically acceptable carrier.

4. The method of claim 1, wherein the subject is a human being and the unmodified soluble CD26 and unmodified soluble Flt-1 are isolated from placental tissues.

5. The method of claim 4, wherein the pharmaceutical composition consists essentially of:
   a) a therapeutically effective amount of unmodified soluble CD26;
   b) a therapeutically effective amount of unmodified soluble Flt-1; and
   c) a pharmaceutically acceptable carrier.

6. The method of claim 4, wherein the pharmaceutical composition consists of:
   a) a therapeutically effective amount of unmodified soluble CD26;
   b) a therapeutically effective amount of unmodified soluble Flt-1; and
   c) a pharmaceutically acceptable carrier.

7. The method of claim 1, wherein the unmodified soluble CD26 inhibits interleukin 2 (IL-2) activity.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Homo sapiens

<400> SEQUENCE: 1

Asn Lys Gly Thr Asp Asp Ala Thr Ala Asp Ser Arg
1               5                   10

<210> SEQ ID NO 2
<211> LENGTH: 9
<212> TYPE: PRT
<213> ORGANISM: Homo sapiens

<400> SEQUENCE: 2

Ala Pro Thr Ser Ser Ser Thr Lys Lys
1               5

<210> SEQ ID NO 3
<211> LENGTH: 13
<212> TYPE: PRT
<213> ORGANISM: Homo sapiens

<400> SEQUENCE: 3

Cys Asn Gly Arg Cys Val Ser Gly Cys Ala Gly Arg Cys
1               5                   10
```